(12) United States Patent
Gayle

(10) Patent No.: US 12,251,115 B2
(45) Date of Patent: Mar. 18, 2025

(54) CLAMP GUARD

(71) Applicant: MAKO Surgical Corp., Weston, FL (US)

(72) Inventor: Carl Gayle, Plantation, FL (US)

(73) Assignee: MAKO Surgical Corp., Weston, FL (US)

(*) Notice: Subject to any disclaimer, the term of this patent is extended or adjusted under 35 U.S.C. 154(b) by 75 days.

(21) Appl. No.: 18/345,680

(22) Filed: Jun. 30, 2023

(65) Prior Publication Data

US 2024/0122608 A1    Apr. 18, 2024

Related U.S. Application Data

(63) Continuation of application No. 17/318,444, filed on May 12, 2021, now Pat. No. 11,730,490.

(60) Provisional application No. 63/023,575, filed on May 12, 2020.

(51) Int. Cl.
| | | |
|---|---|---|
| *A61B 17/14* | (2006.01) | |
| *A61B 90/00* | (2016.01) | |
| *A61B 17/00* | (2006.01) | |

(52) U.S. Cl.
CPC ............ *A61B 17/142* (2016.11); *A61B 90/03* (2016.02); *A61B 2017/00477* (2013.01)

(58) Field of Classification Search
CPC .............................. A61B 17/142; A61B 90/03
See application file for complete search history.

(56) References Cited

U.S. PATENT DOCUMENTS

| | | |
|---|---|---|
| 3,943,934 A | 3/1976 | Bent |
| 4,386,609 A | 6/1983 | Mongeon |
| 5,263,972 A | 11/1993 | Evans et al. |
| 5,265,343 A | 11/1993 | Pascaloff |
| 5,382,249 A | 1/1995 | Fletcher |

(Continued)

FOREIGN PATENT DOCUMENTS

| | | |
|---|---|---|
| DE | 19825408 A1 | 12/1999 |
| DE | 102008037140 A1 | 2/2010 |

OTHER PUBLICATIONS

English language abstract and machine-assisted English translation for DE 198 25 408 A1 extracted from espacenet.com database on Oct. 4, 2021, 13 pages.

(Continued)

*Primary Examiner* — Christian A Sevilla
(74) *Attorney, Agent, or Firm* — Howard & Howard Attorneys PLLC

(57) ABSTRACT

A blade mounting assembly for coupling a saw blade to a surgical saw. The blade mounting assembly including a blade clamp guard and a blade clamp moveably coupled to a drive hub of the surgical saw. The blade clamp guard defining a recess and a blade clamp at least partially disposed within the recess. The blade clamp further comprising a safety indicator. The blade clamp may be configured to move relative to the blade camp guard, the blade clamp moving between a first position where the safety indicator is exposed and a second position where the safety indicator is concealed by the blade clamp guard. The blade mounting assembly may also comprise a biasing mechanism disposed between the blade clamp guard and the blade clamp. The biasing mechanism configured to urge the blade clamp guard away from the blade clamp.

20 Claims, 11 Drawing Sheets

(56) References Cited

U.S. PATENT DOCUMENTS

| | | | |
|---|---|---|---|
| 5,489,285 | A | 2/1996 | Goris |
| 5,729,904 | A | 3/1998 | Trott |
| 5,846,244 | A | 12/1998 | Cripe |
| 5,848,474 | A | 12/1998 | Fortney et al. |
| 6,113,618 | A | 9/2000 | Nic |
| 6,949,110 | B2 | 9/2005 | Ark et al. |
| 8,100,912 | B2 | 1/2012 | Marietta |
| 8,616,562 | B2 | 12/2013 | Maras |
| 8,702,710 | B2 | 4/2014 | Carusillo |
| 8,827,278 | B2 * | 9/2014 | Chen .................. B24B 45/00 451/356 |
| 8,966,772 | B2 | 3/2015 | Legrand et al. |
| 9,149,923 | B2 * | 10/2015 | Campbell ............... B25F 5/003 |
| 9,192,390 | B2 | 11/2015 | delRio et al. |
| 9,346,183 | B2 | 5/2016 | Fankhauser et al. |
| 10,456,142 | B2 | 10/2019 | Shiels |
| 10,667,826 | B2 | 6/2020 | Hassler, Jr. et al. |
| 10,687,824 | B2 | 6/2020 | Shiels et al. |
| 2004/0204731 | A1 | 10/2004 | Gant |
| 2007/0119055 | A1 | 5/2007 | Walen et al. |
| 2008/0027449 | A1 | 1/2008 | Gundlapalli et al. |
| 2009/0312761 | A1 * | 12/2009 | Boykin .................. B27B 5/32 606/82 |
| 2013/0193655 | A1 | 8/2013 | Kaye, Jr. et al. |
| 2013/0204255 | A1 | 8/2013 | Milburn et al. |
| 2013/0204256 | A1 | 8/2013 | Wang et al. |
| 2014/0110908 | A1 | 4/2014 | Fankhauser et al. |
| 2015/0066038 | A1 * | 3/2015 | McGinley .......... A61B 17/1615 606/80 |
| 2015/0182230 | A1 | 7/2015 | Belagali et al. |
| 2017/0282329 | A1 | 10/2017 | Bernardi et al. |
| 2018/0092757 | A1 * | 4/2018 | Behzadi ................. A61F 2/389 |
| 2021/0353303 | A1 | 11/2021 | Gayle |

OTHER PUBLICATIONS

English language abstract and machine-assisted English translation for DE 102 008 037 140 A1 extracted from espacenet.com database on Oct. 4, 2021, 10 pages.

* cited by examiner

CLAMP GUARD

CROSS-REFERENCE TO RELATED APPLICATIONS

The subject application is a continuation of U.S. patent application Ser. No. 17/318,444, filed May 12, 2021, which claims priority to and all benefits from U.S. Provisional Patent Application No. 63/023,575, filed May 12, 2020, the contents of which are hereby incorporated by reference in their entirety.

TECHNICAL FIELD

The configurations described herein generally relate to a blade mounting assembly of a surgical saw including a blade clamp guard.

BACKGROUND

It is prevalent to use powered surgical saws during surgical procedures. Generally, these surgical saws have a handpiece which may include an electric or pneumatic motor disposed within the handpiece. The handpiece may also include a blade mounting assembly for securing a saw blade to the handpiece. The blade mounting assembly may include a driver that is operatively coupled to the motor to be driven by the motor, for example, in an oscillating manner. An attachment portion of a surgical saw blade is releasably coupled to the driver. At the opposite end of the blade is a cutting portion which includes teeth. The driver may comprise one or more driving mechanisms to which the attachment portion of the blade is coupled. When the motor drives the driver, force is applied by the driving mechanism to the attachment portion of the blade, which consequently applies a cutting force to the cutting portion of the blade to cut through material.

Prior surgical saws have contemplated using a clamp to secure the surgical saw blade to the blade mounting assembly. However, with such prior configurations there is a potential that a user can be pinched by the clamp during clamping. Mainly, the prior clamps are non-encapsulated and exposed, and hence, the user is unprotected from the path of the clamping force.

Furthermore, some prior clamps are rigid mechanisms, which when spaced apart from the blade mounting assembly, provide minimal flexibility for installation of the surgical saw blade within the spacing. Also, even when prior clamps are spaced apart from the blade mounting assembly by an amount greater than the thickness of the saw blade, there is a potential that the saw blade can be loosely mounted before clamping because of such extra spacing. Such extra spacing may cause the saw blade to potentially fall out from the surgical saw before clamping and cause harm.

Additionally, prior clamping schemes fail to provide a user with clear indication of full and proper clamping of the saw blade. For example, prior clamping systems may provide a lever that is moveable between an open position wherein the saw blade is not clamped and closed position wherein the saw blade is fully clamped. There is a possibility that the user may not fully engage the lever in the closed position, but the saw blade may appear to be secured. The user may then proceed to operate the tool on the incorrect assumption that the saw blade is properly secured. There is a need to address at least some of these shortcomings of the prior art.

SUMMARY

This Summary introduces a selection of concepts in a simplified form that are further described in the Detailed Description below. This Summary is not intended to limit the scope of the claimed subject matter and does not necessarily identify each and every key or essential feature of the claimed subject matter.

In one aspect, one example of a blade mounting assembly for a surgical saw assembly is provided, wherein the surgical saw assembly comprises a saw blade, a housing, and a driver disposed within the housing configured to couple to a motor and releasably receive and actuate the saw blade, and the blade mounting assembly being coupled to the housing and being configured to releasably clamp the saw blade to the driver, wherein the blade mounting assembly comprises: a clamp guard defining a recess; a blade clamp comprising a safety indicator and being configured to be at least partially disposed within to the recess of the clamp guard, the blade clamp moveable relative to the clamp guard between an exposed position whereby the blade clamp protrudes from the clamp guard such that the safety indicator is visibly exposed and a concealed position whereby the blade clamp is retracted within the recess of the clamp guard such that the safety indicator is concealed by the clamp guard; and a control mechanism configured to move between an open position and a closed position to manipulate the position of the blade clamp between the exposed position and the concealed position, whereby: in the open position, the blade clamp is configured to be in the exposed position such that the safety indicator is exposed, and the blade clamp is spaced apart from the driver by a first distance; and in the closed position, the blade clamp is configured to be in the concealed position such that the safety indicator is concealed, and the blade clamp is spaced apart from the driver by a second distance, wherein the second distance is less than the first distance.

In a second aspect, a surgical saw assembly is provided comprising: a saw blade; a housing; a driver disposed within the housing and being configured to couple to a motor and releasably receive and actuate the saw blade; and a blade mounting assembly coupled to the housing and being configured to releasably clamp the saw blade to the driver, wherein the blade mounting assembly comprises: a clamp guard defining a recess; a blade clamp comprising a safety indicator and being configured to be disposed within and moveable relative to the recess of the clamp guard between an exposed position whereby the safety indicator is visibly exposed and a concealed position whereby the safety indicator is concealed by the clamp guard; and a clamping control mechanism configured to move between an open position and a closed position and being configured to control clamping of the blade clamp, whereby: in the open position, the blade clamp is configured to be in the exposed position such that the safety indicator is exposed, and the blade clamp is spaced apart from the driver by a first distance; and in the closed position, the blade clamp is configured to be in the concealed position such that the safety indicator is concealed, and the blade clamp is spaced apart from the driver by a second distance, wherein the second distance is less than the first distance.

In a third aspect, a blade mounting assembly for attaching a saw blade to a driver is provided. The blade mounting assembly comprises: a clamp guard defining a recess; a clamp member moveably coupled to the driver and configured to move relative to the driver between a first position and a second position; a clamping control mechanism moveable between an open position and a closed position to manipulate the clamp member between the first position and the second position; and a biasing mechanism disposed between the clamp guard and the clamp member, the biasing mechanism configured to urge the clamp guard away from the clamp member such that a distance between the clamp guard and the driver remains constant, or substantially constant, as the clamp member is moved between the first position and the second position; and wherein when the clamping control mechanism is in the open position, the clamp member is configured to be spaced apart from the clamp guard by a first distance and the clamp member at least a portion of the clamp member protrudes from the recess of the clamp guard; and wherein when the clamping control mechanism is in the closed position, the clamp member is configured to be spaced apart from the clamp guard by a second distance and the clamp member is at least partially disposed in the recess of the clamp guard.

Any of the first, second and third aspects can be utilized individually, and in combination.

Any of the first, second and third aspects can also, individually, or in combination, be utilized with any of the following implementations:

In some implementations, a biasing mechanism disposed between the clamp guard and the blade clamp. In some implementations, in the open position, the biasing mechanism is configured to urge the clamp guard away from the blade clamp such that the blade clamp protrudes from the clamp guard to expose the safety indicator. In some implementations, in the closed position, the biasing mechanism is configured to be compressed to allow the blade clamp to be retracted within the recess of the clamp guard and conceal the safety indicator.

In some implementations, the driver comprises: a platform configured to support an attachment portion of the saw blade. In some implementations, the driver comprises: at least one drive member adapted to be coupled to the attachment portion of the saw blade and being configured to be actuated by the driver. In some implementations, the at least one drive member is protruding from a plane of the platform of the driver.

In some implementations, in the open position, the blade mounting assembly is configured to operate in an at-rest state wherein the attachment portion of the saw blade is not inserted into the blade mounting assembly. In some implementations, in the at-rest state, the biasing mechanism is configured to urge the clamp guard away from the blade clamp such that the clamp guard remains proximal the at least one drive member when the blade clamp is spaced the first distance from the driver.

In some implementations, in the open position, the blade mounting assembly is configured to operate in an insertion state wherein the attachment portion of the saw blade is partially inserted into the blade mounting assembly such that the attachment portion of the saw blade is wedged between the clamp guard and the at least one drive member. In some implementations, in the insertion state, the biasing mechanism is configured to be compressed allowing the clamp guard to move from being spaced a third distance from to the driver to a fourth distance from the driver as the attachment portion is wedged between the clamp guard and the at least one drive member.

In some implementations, in the open position, the blade mounting assembly is configured to operate in a secured state wherein the attachment portion of the saw blade is fully inserted into the blade mounting assembly such that the attachment portion of the saw blade is supported by the platform and coupled to the at least one drive member. In some implementations, in the secured state, the biasing mechanism is configured to urge the clamp guard to directly abut the attachment portion of the saw blade.

In some implementations, in the open position, the blade mounting assembly is configured to operate in an at-rest state wherein the attachment portion of the saw blade is not inserted into the blade mounting assembly. In some implementations, in the at-rest state, the biasing mechanism is configured to be compressed to a fifth distance between the clamp guard and the blade clamp.

In some implementations, in the open position, the blade mounting assembly is configured to operate in an insertion state wherein the attachment portion of the saw blade is partially inserted into the blade mounting assembly such that the attachment portion of the saw blade is wedged between the clamp guard and the at least one drive member. In some implementations, in the insertion state, the biasing mechanism is configured to be compressed to a sixth distance between the clamp guard and the blade clamp, wherein the sixth distance is less than the fifth distance.

In some implementations, in the open position, the blade mounting assembly is configured to operate in a secured state wherein the attachment portion of the saw blade is fully inserted into the blade mounting assembly such that the attachment portion of the saw blade is supported by the platform and coupled to the at least one drive member. In some implementations, in the secured state, the biasing mechanism is configured to be compressed to a seventh distance between the clamp guard and the blade clamp, wherein the seventh distance is less than or equal to the fifth distance.

In some implementations, in the closed position, the biasing mechanism is configured to compress to an eighth distance between the clamp guard and the blade clamp, wherein the eighth distance is less than each of the fifth, sixth, and seventh distances.

In some implementations, the blade clamp comprises an upper surface, a lower surface and a clamp side surface disposed between the upper and lower surfaces. In some implementations, the safety indicator is disposed on the clamp side surface of the blade clamp. In some implementations, the clamp guard comprises a primary surface and a guard side surface that define the recess of the clamp guard. In some implementations, in the exposed position, the lower surface of the blade clamp is configured to be spaced apart from the primary surface of the clamp guard and concealed by the guard side surface of the clamp guard and the clamp side surface of the blade clamp is configured to be exposed. In some implementations, in the concealed position, the lower surface of the blade clamp is configured to abut the primary surface of the clamp guard and the guard side surface is configured to conceal the clamp side surface of the blade clamp.

In some implementations, the blade clamp comprises at least one notch defined on the side surface of the blade clamp and between the upper and lower surfaces. In some implementations, the clamp guard defines at least one opening in the primary surface. In some implementations, in the concealed position, the at least one opening is configured to receive a portion of at least one drive member adapted to be coupled to the attachment portion of the saw blade. The at least one drive member may be configured to align and/or orient the saw blade. The at least one drive member may also be configured to be actuated by the driver to actuate the saw blade.

In some implementations, a biasing mechanism disposed between the clamp guard and the clamp member, the biasing mechanism configured to urge the clamp guard away from the clamp member. In some implementations, the biasing mechanism does so such that a distance between the clamp guard and the driver remains constant as the clamp member is moved between the first position and the second position. In some implementations, the biasing mechanism is coil spring.

In some implementations, the safety indicator is a visual indicator. In some implementations, the safety indicator comprises a colored band or bands. In some implementations, the safety indicator band(s) is/are colored red. In some implementations, the safety indicator comprises indicia, graphics, or text. In some implementations, the safety indicator comprises an electronic component(s) or a device configured to emit light to provide visual indication. In some implementations, the safety indicator comprises an LED ring. In some implementations, the safety indicator comprises a device configured to provide an audible feedback.

In some implementations, the saw blade is a sagittal saw or oscillating saw. In some implementations, the saw blade is a reciprocating saw or a rotary saw. In some implementations, the clamping assembly can be utilized to clamp accessories other than a saw blade. In some implementations, the accessory can be a drill bit, a driver probe, a burr, or impactor accessory. In some implementations, the clamping assembly can be utilized with powered tools other than powered saw tools. For example, the powered tool can be a drill, driver, or impactor. Furthermore, in some implementations, the clamping assembly is utilized with a hand-held tool. In some implementations, the clamping assembly is utilized with an end effector assembly that is attachable to robotic manipulator.

These and other configurations, features, and advantages of the present disclosure will be apparent to those skilled in the art. The present disclosure is not to be limited to or by these configurations, features, and advantages.

BRIEF DESCRIPTION OF THE DRAWINGS

Referring now to the drawings, exemplary illustrations are shown in detail. Although the drawings represent schematic configurations, the drawings are not necessarily to scale and certain features may be exaggerated to better illustrate and explain an innovative aspect of an illustrative configuration. Further, the exemplary illustrations described herein are not intended to be exhaustive or otherwise limiting or restricting to the precise form and configuration shown in the drawings and disclosed in the following detailed description.

Advantages of the present disclosure will be readily appreciated as the same becomes better understood by reference to the following detailed description when considered in connection with the accompanying drawings.

DETAILED DESCRIPTION

Figure 1:
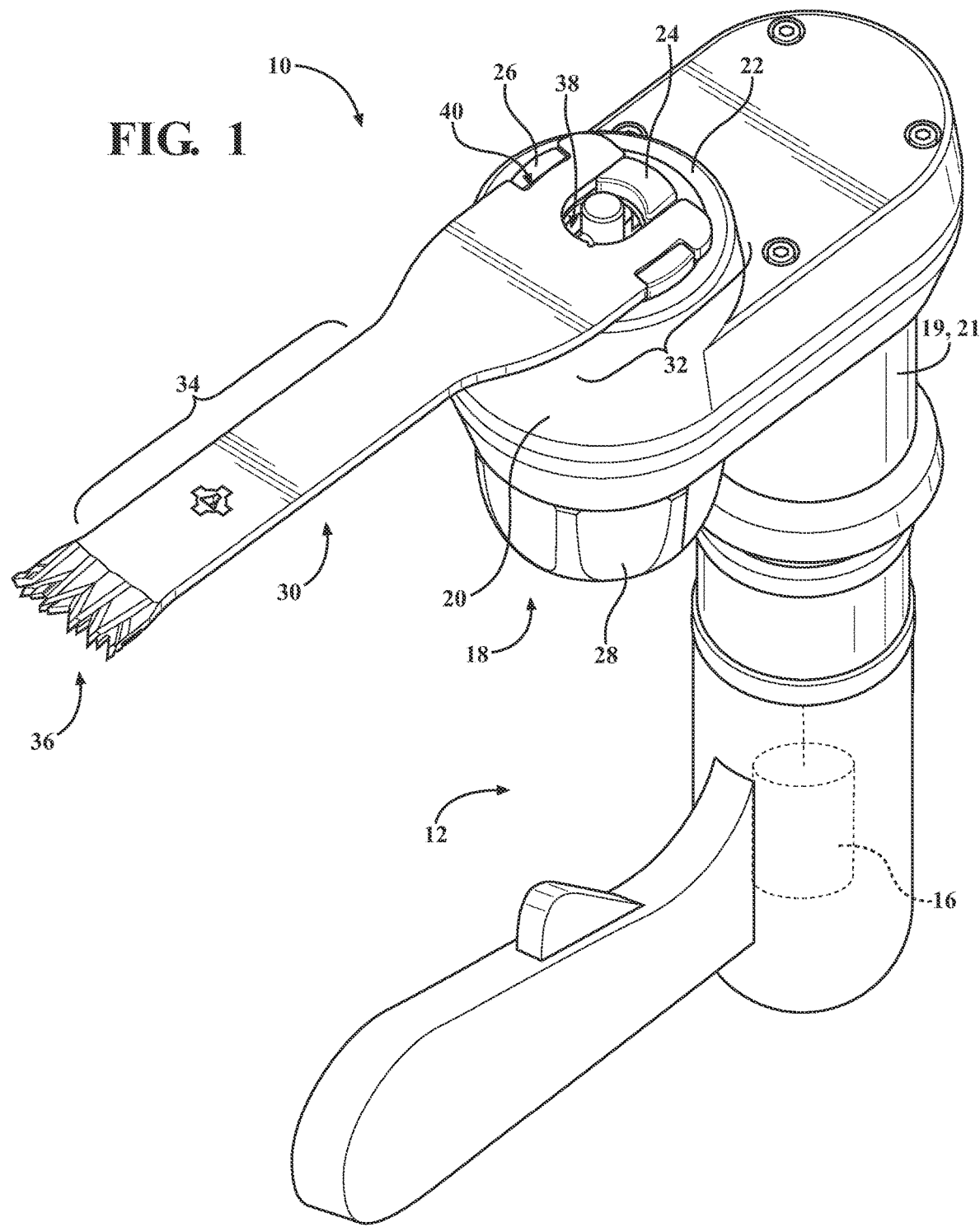
FIG. 1 is a perspective view of a surgical saw assembly including a blade mount assembly for securing a saw blade, according to one implementation.
Figure 2:
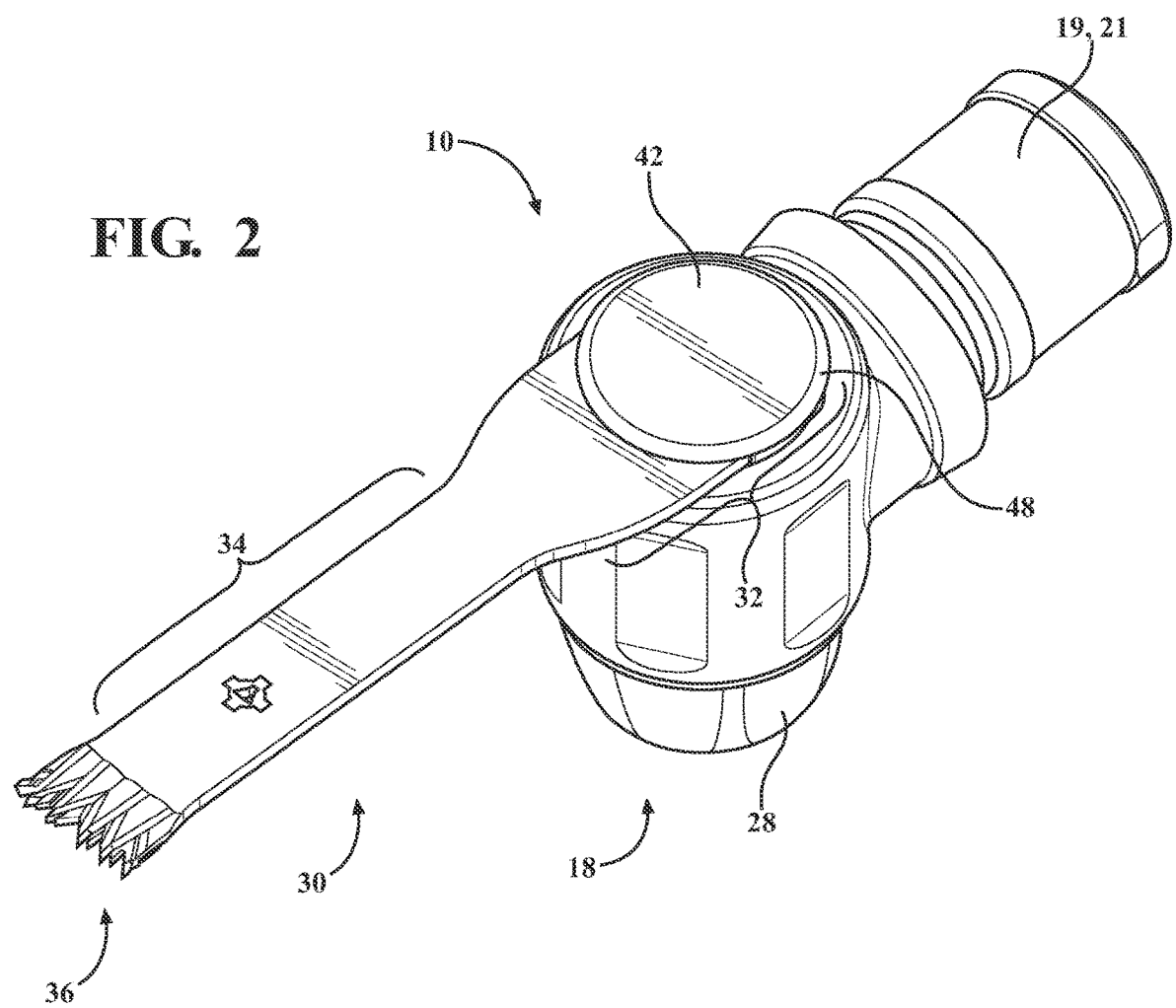
FIG. 2 is a perspective view of another implementation of the blade mount assembly and the saw blade of the surgical saw assembly, wherein a cap is further provided.

Referring to FIGS. 1 and 2, a tool 10 is disclosed, wherein in one example, the powered tool 10 is a surgical saw assembly. The tool 10 is for use during surgical procedures. The surgical procedures may be orthopedic surgeries, brain surgeries, cardiovascular surgeries or any other surgeries requiring the use of an energy applicator. Tools other than the saw assembly, including, but not limited to, drills, drivers, impactors, reamers or the like, are contemplated for use.

An accessory 30 is coupled to the tool 10. In one implementation, the accessory is a surgical saw blade 30. The blade 30 may be of various shapes and sizes such as a crescentic blade or a straight blade. The saw blade 30 can be a sagittal saw, reciprocating saw, rotary saw, or any other configuration of saw blade. Furthermore, accessories other than saw blades, including but not limited to, drill bits, driver probes, impactor accessories, reamer accessories or the like, are contemplated for use.

The tool 10 can attach to a powered device 12. In one example, the powered device 12 can be an end effector of a surgical robotic manipulator (not shown) or the combination of the end effector and the robotic manipulator. The robotic manipulator comprises a plurality of joints and joint actuators forming an arm that is configured to move in multiple degrees of freedom. In other configurations, the powered device 12 is a hand-held powered tool, such as a hand-held powered saw, drill, impactor or reamer. In one example, the hand-held powered tool is supported by the arm and hand of the operator against the force of gravity. In other examples, the hand-held powered tool can be attached to and supported by a passive linkage assembly that is coupled to the patient or surgical table. For simplicity, the tool 10 and accessory 30 are the saw assembly 10 and saw blade 30 in the description below.

The saw assembly 10 shown in FIG. 1 has a coupler 19 for attaching to the powered device 12. The coupler 19 can be a right-angle type or a straight type, as shown in FIG. 2. The coupler 19 comprise a housing 21 for attaching to the powered device 12. The housing 21 can include any components for attaching to the powered device 12 as well as any components of the saw assembly 10, generally. A motor 16 may be located in the powered device 12 (as shown), in the housing 21 attached to the powered device 12, or in a sub-system located remote from the powered device 12. The motor 16 may be of any suitable type, including but not limited to a pneumatic or electrical motor. The motor 16 is configured to provide oscillating motion to the saw blade 30. It is contemplated that the motor 16 may provide cyclical linear motion and/or cyclical angular motion, such as used for an oscillating sagittal saw.

The motor 16 is operatively coupled to a driver 20. The driver 20 transfers drive torque from the motor 16 to the saw blade 30. The driver 20 is at least partially disposed within the housing 21 and includes a drive hub 22. The drive hub 22 is configured to releasably receive the saw blade 30. As illustrated in FIG. 1, the drive hub 22 may include one or more primary drive bosses 24 or drive members adapted to engage the saw blade 30. The driver 20, including the drive hub 22, may oscillate due to torque from the motor 16 which in turn will oscillate the saw blade 30 about a rotation axis. In addition to the drive hub 22, the driver 20 comprises additional components to convert torque from a drive shaft of the motor 16 into oscillating motion of the drive hub 22. Examples of such components are shown and described in U.S. Pat. No. 8,100,912 to Marietta, hereby incorporated by reference. In other configurations, the drive shaft of the motor 16 may directly drive the drive hub 22 to rotate the drive hub 22 and may oscillate the drive hub 22 or rotate the drive hub 22 in complete rotations in one direction and/or another.

Referring to FIGS. 1 and 2, the saw blade 30 includes an attachment portion 32 configured to be removably coupled to the drive hub 22. Opposite the attachment portion 32, the saw blade 30 includes a cutting portion 36 which has a plurality of teeth. A body portion 34 extends between the attachment portion 32 and the cutting portion 36. The attachment portion 32 of the saw blade 30, in the configuration shown, generally has a width greater than a width of the cutting portion 36. In some configurations, the saw blade 30 is formed from a single piece of material, such as metal, by stamping and/or machining.

The attachment portion 32 includes a tapered section which gradually gets narrower until it reaches a transition section. Opposite the transition section from the attachment portion 32 is the body portion 34. The body portion 34 may have a continuous width from the transition section to the cutting portion 36. It is also contemplated that the body portion 34 may gradually get narrower in width as the body portion 34 approaches the cutting portion 36. In other configurations, the body portion 34 may gradually get wider in width as the body portion 34 approaches the cutting portion 36. Outer side surfaces of the saw blade 30 at the attachment portion 32 and the body portion 34 may be perpendicular to top and bottom surfaces of the saw blade 30.

It is contemplated that the length of the attachment portion 32 is less than the length of the body portion 34, however, many other configurations have been contemplated. Moreover, the length of the cutting portion 36 may be less than the length of the attachment portion 32 and less than the length of the body portion 34. As illustrated, the body portion 34 is generally elongate and rectangularly shaped while at least a portion of the attachment portion 32 may include curves. It is also contemplated that the attachment portion 32 and/or the body portion 34 may be of various other configurations.

Moreover, as best shown in FIGS. 1 and 2, the body portion 34 may reach a second transition section which is disposed between the body portion 34 and the cutting portion 36. The second transition section may have a different, typically smaller, width than the width of the teeth and the width of the body portion 34. It is also contemplated that the second transition section may taper inwards from the body portion 34 before once again tapering outwards towards the teeth of the cutting portion 36.

As best illustrated in FIG. 1, the saw blade 30 defines primary indents 40 on the attachment portion 32. The primary indents 40 are disposed on opposite lateral sides of the attachment portion 32 and are disposed through the thickness of the saw blade 30. Each of the primary indents 40 are defined by a first side, a second side, and a third side with the first and third side being generally perpendicular to the second side. Moreover, the second side is disposed between the first side and the third side. In the configuration shown, the second side 4 is integral and smoothly continuous with the first side and the third side by virtue of rounded profile transitions therebetween, described further below. An indent space is formed by the first side, the second side, and the third side.

Additionally, the saw blade 30 includes a central indent 38. The central indent 38 is generally 'U' shaped and has a free space disposed between the primary indents 40 about the rotational axis. The central indent 38 may also include a notch. The notch may be configured to engage a portion of the drive hub 22, such as a smaller boss (not shown) protruding upwardly into the notch. The notch may be disposed off-center or to one side of center of the central indent 38 so that the saw blade 30 is properly fitted with the top surface facing upwardly. Other configurations are contemplated. It is also contemplated that the notch may be disposed along any portion of the central indent 38. An example of such a saw blade for use with the blade mounting assembly 18 and/or the surgical saw system 10 is shown and described in U.S. Pat. No. 10,456,142 to Shiels, hereby incorporated by reference.

Figure 3:
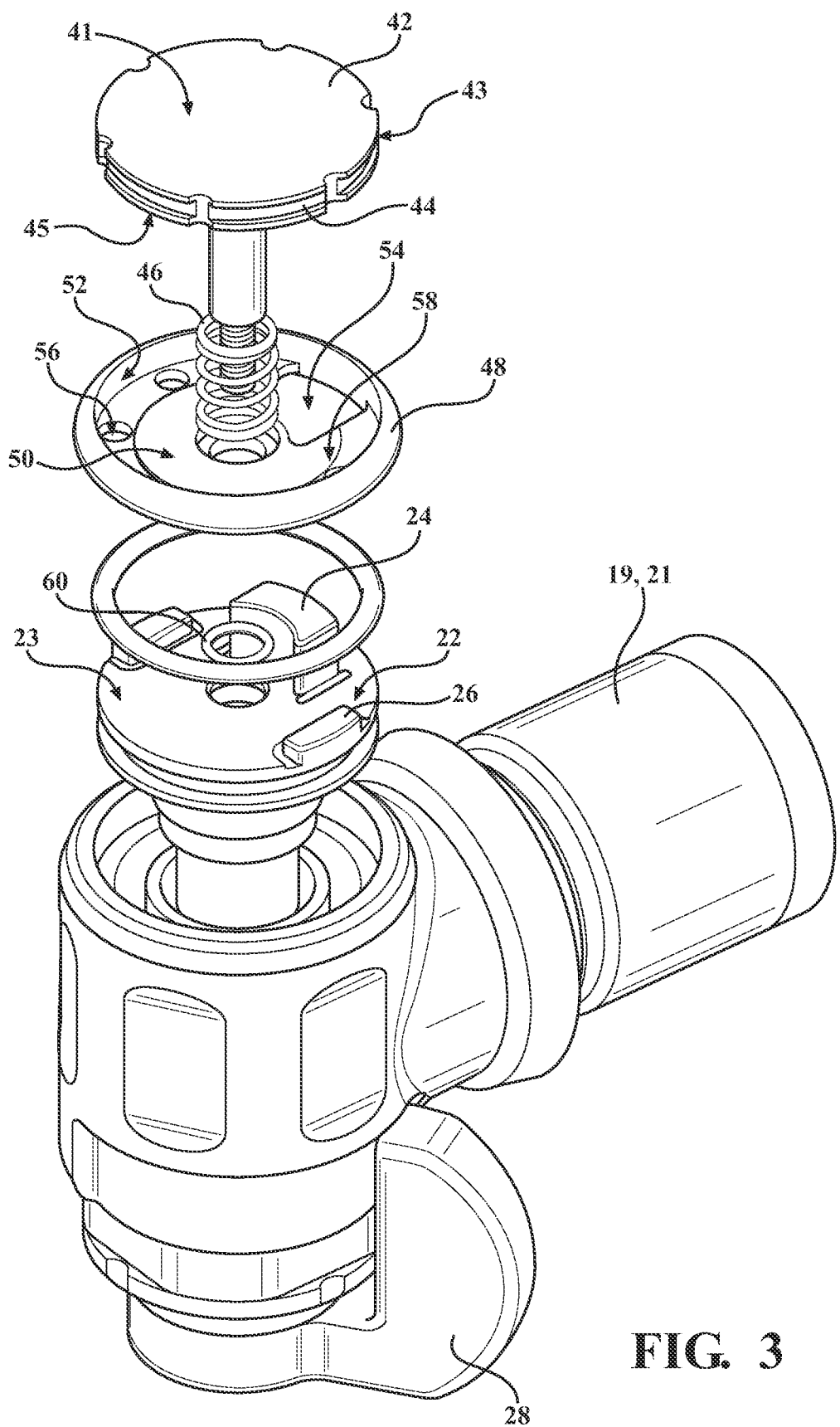
FIG. 3 is a partially exploded view of the blade mount assembly of the surgical saw assembly, according to one implementation.

Referring now to FIG. 3, a partially exploded view of the blade mounting assembly 18 is illustrated. The drive hub 22 has a generally circular outer periphery and includes the primary drive bosses 26. The drive hub 22 also includes a generally circular opening disposed in the center of the drive hub 22. In the illustrated configuration, the drive hub 22 includes two primary drive bosses 26 disposed opposite to one another, but identical in configuration. Each of the primary drive bosses 26 protrude radially inwardly from the outer periphery of a support surface 23 of the drive hub 22. Additionally, the drive hub 22 includes a central drive boss 24 disposed partially about the circular opening. Aside from the drive bosses 24, 26, the drive hub 22 has a generally flat support surface 23 adjacent to the drive bosses 24, 26 on which the flat bottom surface of the attachment portion 32 of the saw blade 30 is supported. The support surface 23 may also be referred to as a platform. The drive bosses 24, 26 may project and/or extend from the support surface 23.

In the configuration of the blade mounting assembly 18 illustrated in FIG. 3, the primary drive bosses 26 have a first surface, a second surface, and a third surface which are generally flat, with the first and third surfaces disposed parallel to one another. The primary drive bosses 26 also have an outer fourth surface that is continuous with the outer periphery. On the central drive boss 24, opposite first and second surfaces are flat in shape while a third surface, disposed about the circular opening, is arcuate and identical in shape to a fourth surface. It is contemplated that various other shapes and sizes of drive bosses 26 are possible.

As illustrated in FIGS. 1 and 3, the drive bosses 26 on the drive hub 22 are adapted to be removably placed within the primary indents 38, 40 of the saw blade 30 when the saw blade 30 is attached to the drive hub 22. In the configuration illustrated in FIG. 1, the primary indents 40 are configured to receive the primary drive bosses 26 and the central indent 38 is configured to receive the central drive boss 24. When the saw blade 30 is coupled to the corresponding drive bosses 24, 26 at the primary indents 38, 40, the driver 20 translates motion from the motor 16 to the saw blade 30, and moves the saw blade 30 in an oscillating motion to allow the plurality of teeth of the cutting portion 36 to cut during a surgical procedure. It is contemplated that in one configuration of the driver 20, the primary diver boss(es) 26 may be configured to articulate the saw blade 30 and the central drive boss 24 may be configured to align the saw blade 30 within the blade mounting assembly 18. Alternatively, it is also contemplated that the driver 20 may be configured such that the central diver boss 24 is configured to articulate the saw blade 30 and the primary drive boss(es) 26 may be configured to align the saw blade 30 within the blade mounting assembly 18. In yet another configuration, the driver 20 may be configured such that both the primary diver boss(s) 26 and/or the central drive boss 24 are configured to articulate the saw blade 30 and to align the saw blade 30 within the blade mounting assembly 18.

The blade mounting assembly 18 may further comprise a blade clamp 42. As illustrated in FIG. 2, the saw blade 30 may be secured to the drive hub 22 using a blade clamp 42. The blade clamp 42 is adapted to be moveably coupled to the drive hub 22 such that the saw blade 30 may be disposed between the drive hub 22 and the blade clamp 42. The blade clamp 42 may comprise a top surface 41, a bottom surface 45, and a side surface 43 disposed between the top 41 and bottom surfaces 45. The blade clamp 42 may be round as illustrated in FIGS. 2 and 3. While not illustrated in the figures, it is contemplated that the blade clamp 42 may comprise any shape, including oval or rectangular. It is contemplated that the blade clamp 42 is configured to move between a first position and a second position relative to the support surface 23 of the drive hub 22 as part of attaching, securing, and removing the saw blade 30 to the drive hub 22. For example, the first position may be defined by the blade clamp 42 being spaced a first distance D1 from the support surface 23 of the drive hub 22. The second position may be defined by the blade clamp 42 being spaced a fifth distance D5 (as shown in FIG. 7B) from the support surface 23 of the drive hub 22. These configurations will be described in more detail below. The first position may also be referred to as an open position or an exposed position, and the second position may be referred to as a closed position or a concealed position. The blade clamp 42 may be friction fitted onto the drive hub 22 or other portion of the driver 20 or may be secured by other mechanisms. The blade clamp 42 has been removed in FIG. 1 for to purpose of illustration.

The side surface 43 of the blade clamp 42 may comprise a safety indicator 44 configured to allow the user to identify whether the blade clamp 42 is in the first position of the second position. The safety indicator 44 may comprise a distinct color different from the rest of the blade clamp 42 and/or the other features of the blade mounting assembly 18. For example, the safety indicator 44 may include red or yellow marking on the side surface of the blade clamp 42. Alternatively, the safety indicator 44 may comprise a text, symbols, lights, or other similar indicia intended to get the user attention and notify them of the position the blade clamp 42 is in. Furthermore, the blade clamp 42 may be configured such that the safety indicator 44 is exposed when the blade clamp 42 is in the first position and the safety indicator 44 is concealed when the blade clamp 42 is in the second position, or vice versa. For example, the blade clamp 42 may be configured such that the safety indicator 44 is exposed when the blade clamp 42 is in the first position to notify the user the surgical saw assembly 10 is not safe to use because the blade clamp 42 is in the open or loading position suggesting the blade is not secured and/or locked into the blade mounting assembly 18. Alternatively, the blade clamp 42 may be configured such that the safety indicator 44 is concealed when the blade clamp 42 is in the second position because the surgical saw assembly 10 is safe to use because the blade clamp 42 is in the closed or locked position and the blade is properly secured and/or locked into the blade mounting assembly 18.

The blade mounting assembly 18 may further comprise a control mechanism 28 moveable between and open position and a closed position. The control mechanism 28 may be manipulatable by the user of the surgical saw assembly 10 move the blade clamp between the first position and the second position. For example, the control mechanism 28 may be configured such that when the control mechanism 28 is in the open position, the blade clamp 42 is in the first position for loading or removing a saw blade 30 from the blade mounting assembly 18. Alternatively, the control mechanism 28 may be configured such that when the control mechanism 28 is in the closed position, the blade clamp 42 is in the second position and the saw blade 30 is secured and/or locked into the blade mounting assembly 18. The control mechanism 28 may comprise a rotary knob (as shown in FIG. 1), lever (as shown in FIGS. 3-7), switch, button, or similar electromechanical device capable of manipulating the blade clamp 42 between the first position and the second position.

The blade mounting assembly 18 may further comprise a clamp guard 48. The clamp guard 48 may be disposed between the blade clamp 42 and the drive hub 22. The clamp guard may comprise a primary surface 50 and a side surface 52. The primary surface 50 may comprise one or more apertures 54, 56. At least of the apertures 56 may be configured to receive at least a portion of the primary drive boss 24. The side surface 52 of the clamp guard 48 may extend from the perimeter of the primary surface 50 such that the side surface encircles the primary surface 50. Furthermore, the primary surface 50 and the side surface 52 may define a recess 58. The recess 58 may be configured to receive at least a portion of the blade clamp 42. For example, when the blade clamp 42 is in the second position, the blade mounting assembly 18 may be configured such that the blade clamp 42 is retracted within the recess 58 defined by the clamp guard 48. Furthermore, the clamp guard 48 may be configured to conceal the safety indicator 44 disposed on the blade clamp 42 when the blade clamp 42 is in the second position and retracted within the recess 58. Alternatively, when the blade clamp 42 is in the first position, the blade mounting assembly 18 may be configured such that the blade clamp 42 protrudes from the recess 58 defined by the clamp guard 48, exposing the safety indicator 44.

The blade mounting assembly 18 may further comprise a biasing mechanism 46 or biasing member disposed between the blade clamp 42 and the clamp guard 48. The biasing mechanism 46 may be configured to urge the clamp guard 48 away from the blade clamp 42. When the blade clamp 42 is in the first position and spaced a first distance D1 from the support surface 23 of the drive hub 22, the biasing mechanism 46 may urge the clamp guard 48 away from the blade clamp 42 and toward the support surface 23 of the drive hub 22. The force exerted by the biasing mechanism 46 on the clamp guard 48 is sufficient to urge the clamp guard 48 away from the blade clamp 42 allowing the blade clamp to protrude from and/or be exposed from the recess 58 of the clamp guard 48, but the force is not so great that it cannot be overcome by a greater force action on the clamp guard 48 in the opposite direction. For example, exerting a force greater than the biasing mechanism 46 on the clamp guard in the opposing direction could cause the clamp guard to be move and reducing the distance between the clamp guard 48 and the blade clamp 42. Alternatively, when the blade clamp 42 is in the second position and spaced a fifth distance D5 from the support surface 23 of the drive hub 22, the biasing mechanism 46 may be compressed as the blade clamp 42 is pulled toward the support surface 23 of the drive hub 22, with the clamp guard 48 being wedged between the blade clamp 42 and drive boss(es) 24, 26 and/or the support surface 23 of the drive hub 22. When the blade clamp 42 is in the second position and the biasing mechanism 46 may be compressed reducing the distance between the blade clamp 42 and the clamp guard 48, a portion of the central drive boss 24 may be at least partially disposed in the aperture 54 in the primary surface 50 of the clamp guard 48. The biasing mechanism 46 allows the clamp guard to float between the blade clamp 42 and the support surface 23 of the drive hub 22 as the blade clamp 42 moves between the first position and the second position.

Figure 4A:
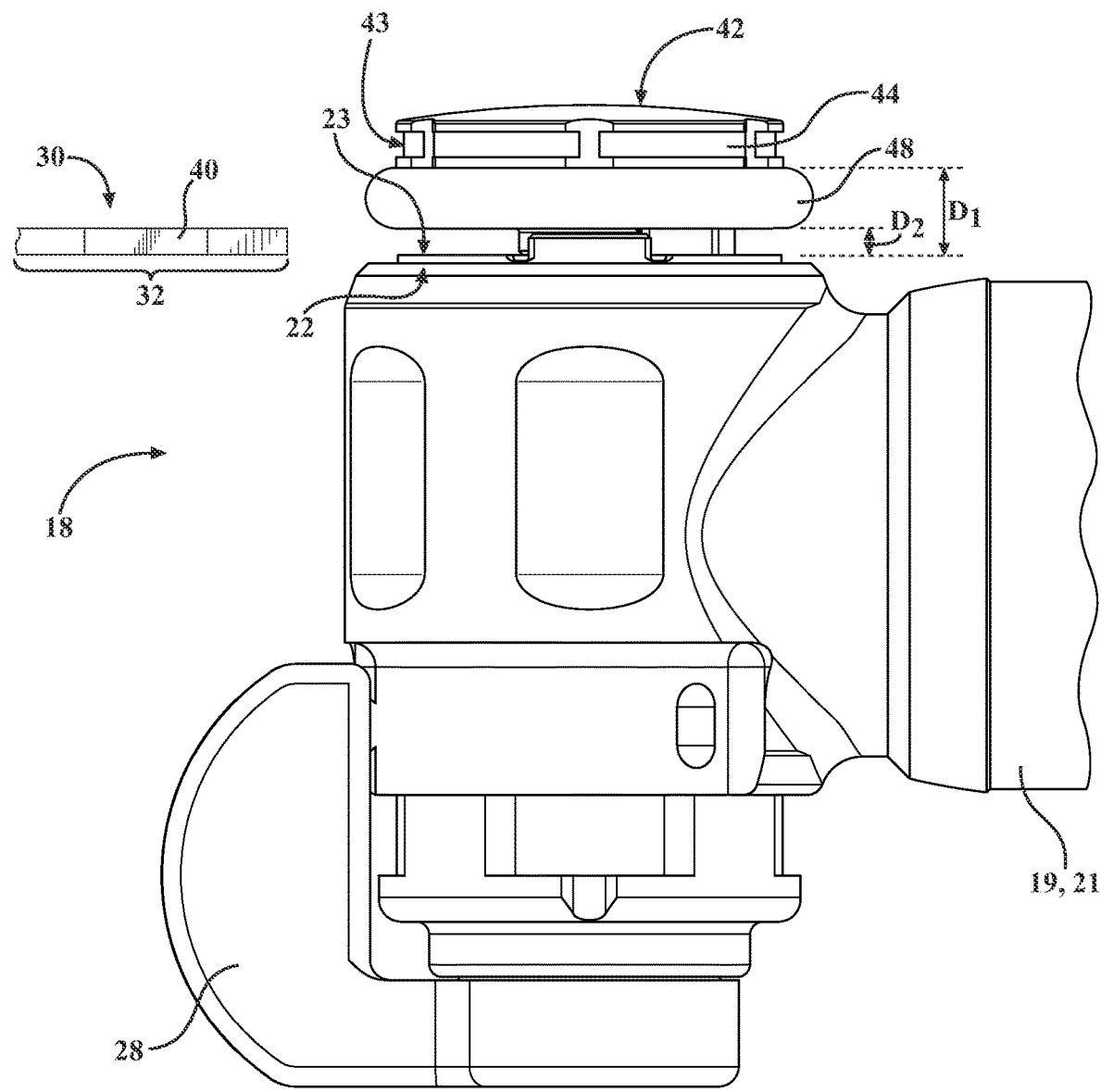
FIG. 4A is a side view of a blade mounting assembly including a blade clamp in an exposed position prior to insertion of a saw blade, according to one implementation.
Figure 4B:
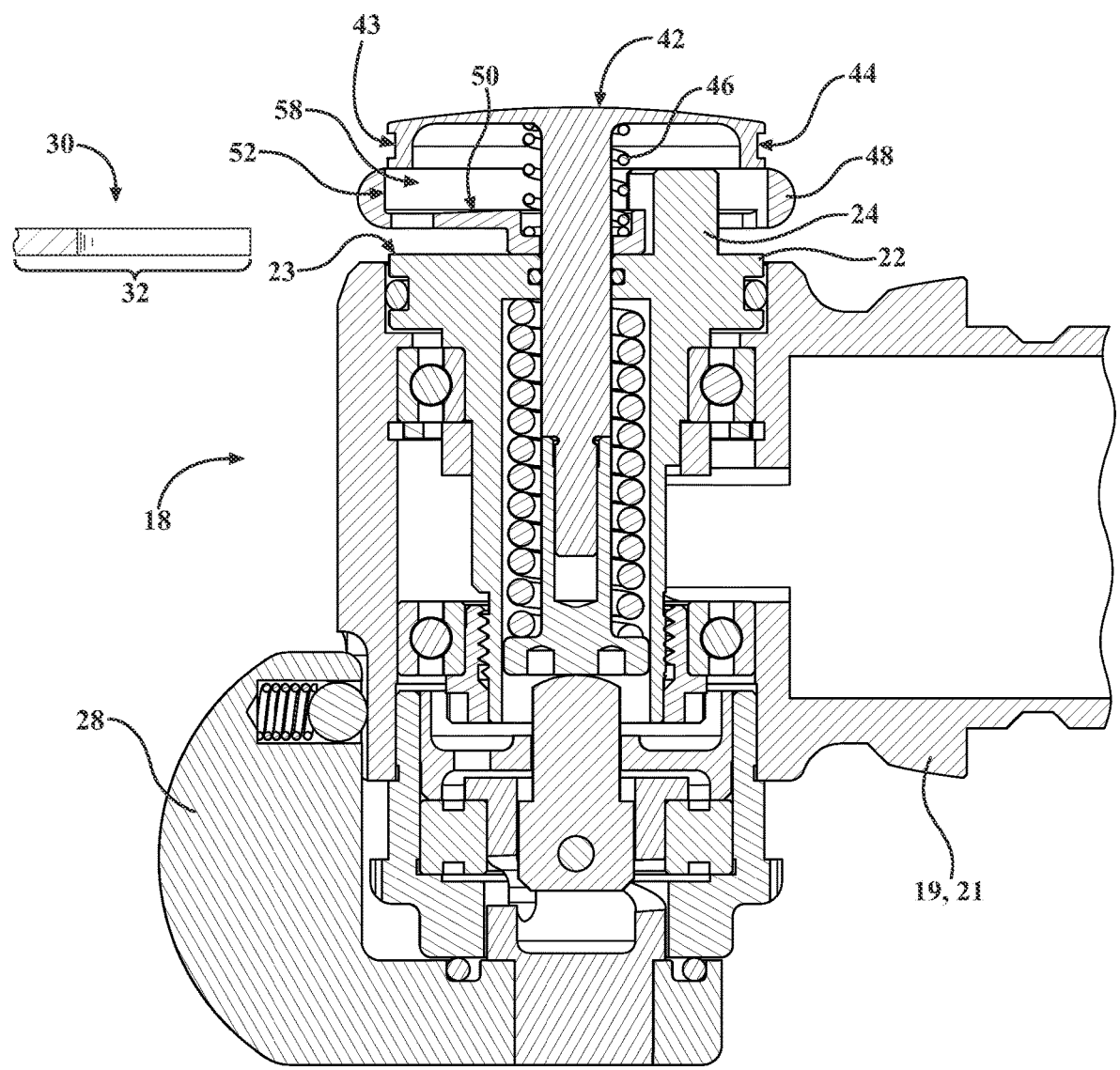
FIG. 4B is a sectional view of the blade mounting assembly and blade of FIG. 4A.

Referring to FIGS. 4A and 4B, an exemplary configuration of the blade mounting assembly 18 in an at-rest state is illustrated. This may also be referred to as an open state. The control mechanism is in the open position causing the blade clamp 42 to be in the first position. As described above, when the blade clamp 42 is in the first position, the blade clamp is spaced a first distance D1 from the support surface 23 of the drive hub 22. The biasing mechanism 46 is configured to urge the clamp guard 48 away from the blade clamp 42 and toward the support surface 23 of the drive hub 22 such that the clamp guard 48 is spaced a second distance D2 from the support surface 23 of the drive hub 22. As the biasing mechanism 46 urges the clamp guard 48 away from the blade clamp 42 and toward the support surface 23, the blade clamp 42 protrudes from the recess 58 of the clamp guard 48 exposing the safety indicator 44. This notifies the user that the surgical saw assembly 10 is not ready for use. In the at-rest state, the blade mounting assembly 18 is ready to receive the attachment portion 32 of the saw blade 30, but the saw blade has not engaged the blade mounting assembly 18 yet.

Figure 5A:
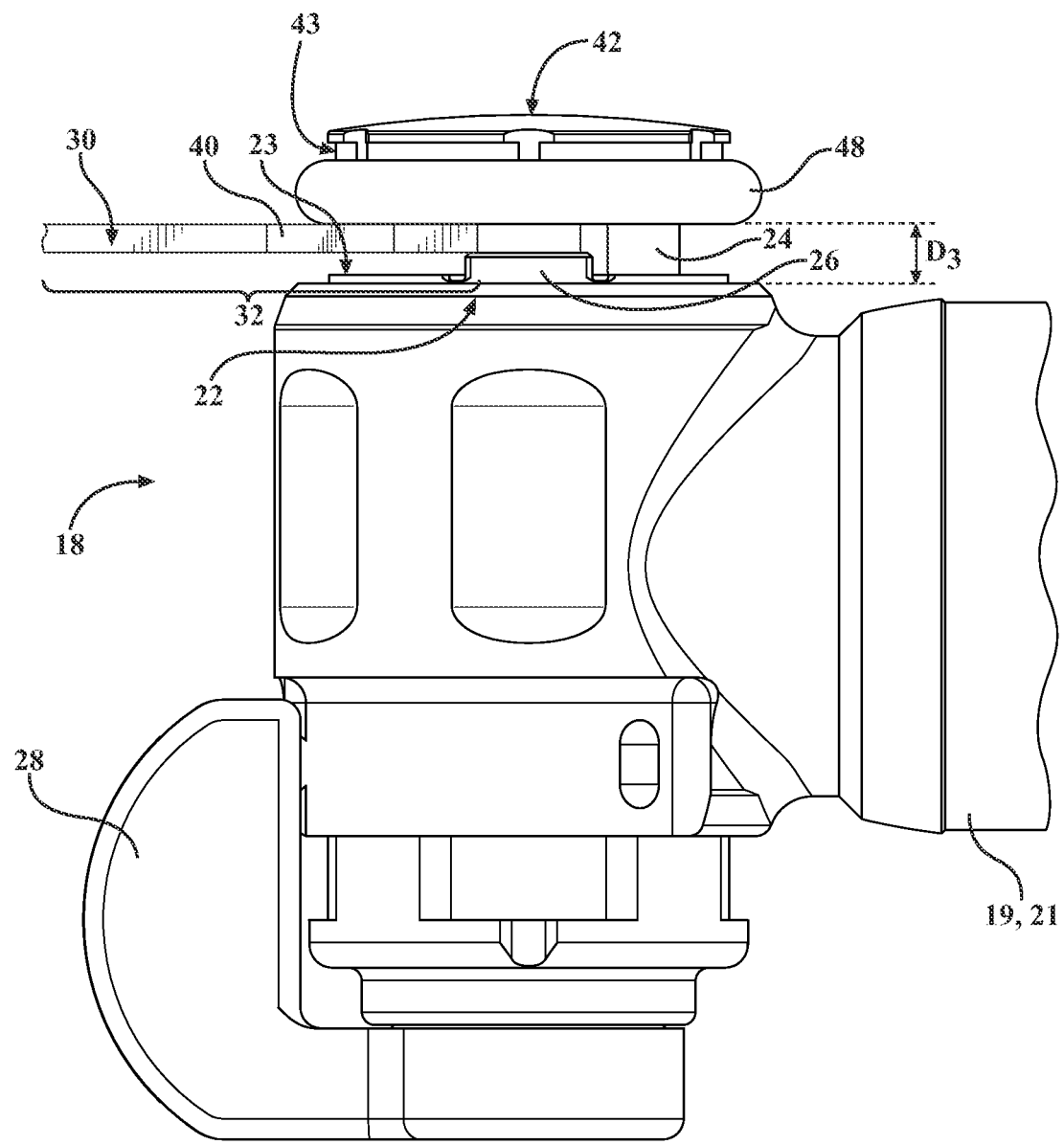
FIG. 5A is a side view of the blade mounting assembly including the blade clamp in the exposed position and the saw blade partially inserted into the blade mounting assembly, according to one implementation.
Figure 5B:
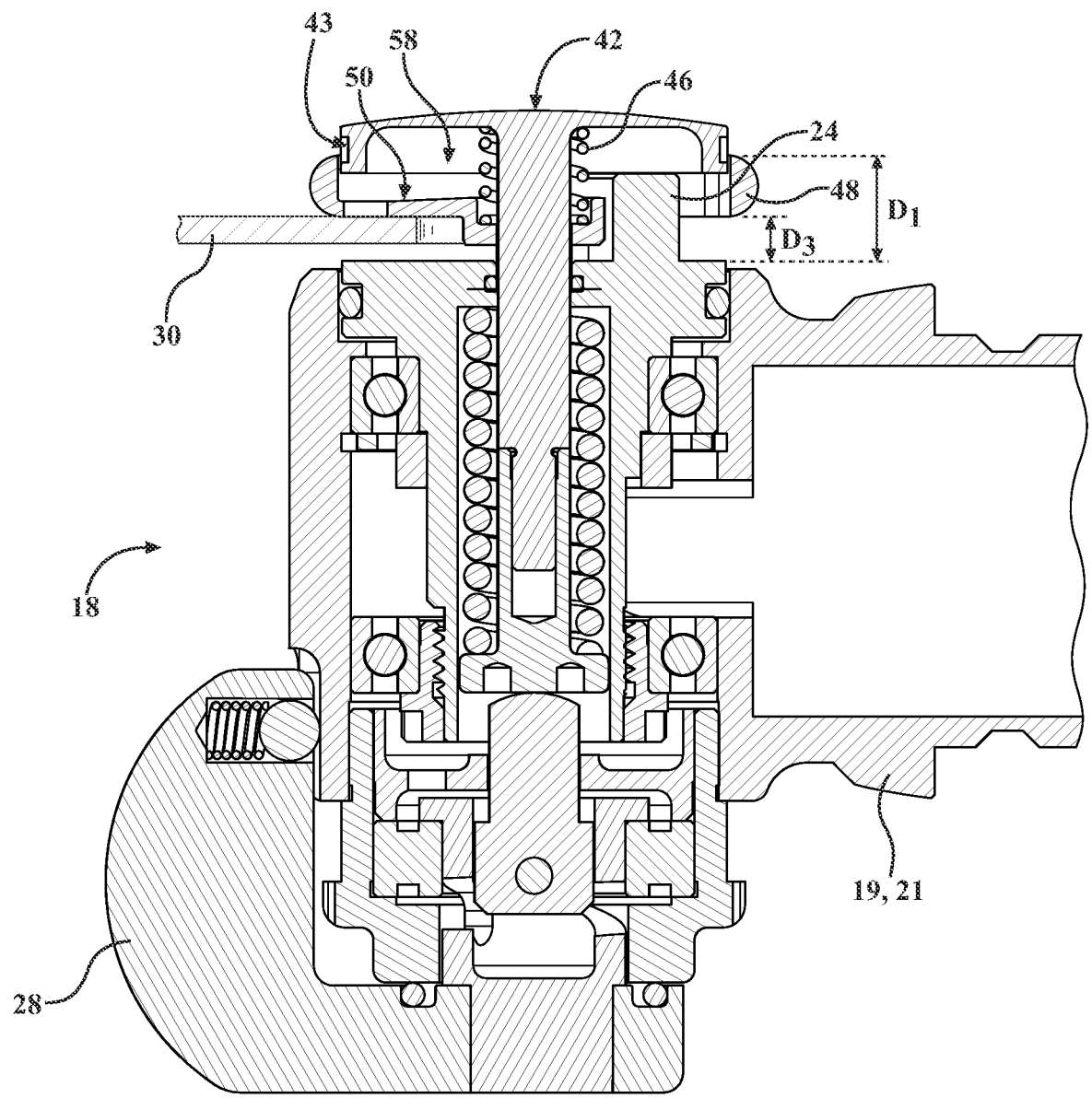
FIG. 5B is a sectional view of the blade mounting assembly and blade of FIG. 5A.

Referring to FIGS. 5A and 5B, an exemplary configuration of the blade mounting assembly 18 in an insertion state is illustrated. This may also be referred to as a loading or mounting state. Similar to when in the at-rest state, the control mechanism 28 is in the open position and the blade clamp 42 is in the first position. When the blade mounting assembly 18 is in the insertion state, at least a portion of the attachment portion 32 of the saw blade 30 is inserted into the blade mounting assembly 18. When inserting the saw blade 30, the attachment portion 32 is wedged between the drive boss(es) 26 and the clamp guard 48. As the drive boss(es) 26 are stationary and/or fixed, wedging the attachment portion 32 between the drive boss(es) 26 and the clamp guard 48 causes a force to be applied to the clamp guard 48 in the opposite direction of the biasing mechanism 46. This results in the clamp guard 48 being spaced a third distance D3 from the support surface 23 of the drive hub 22, such that the third distance D3 is greater than the second distance D2. Expressed another way, wedging the attachment portion 32 between the drive boss(es) 26 and the clamp guard 48 causes a force to be applied to the clamp guard 48 in the opposite direction of the biasing mechanism 46, causing the biasing mechanism 46 to be compressed and the distance between the clamp guard 48 and the blade clamp 42 to be reduced. This allows the attachment portion 32 of the saw blade 30 to be inserted over the drive boss(es) 26

Figure 6A:
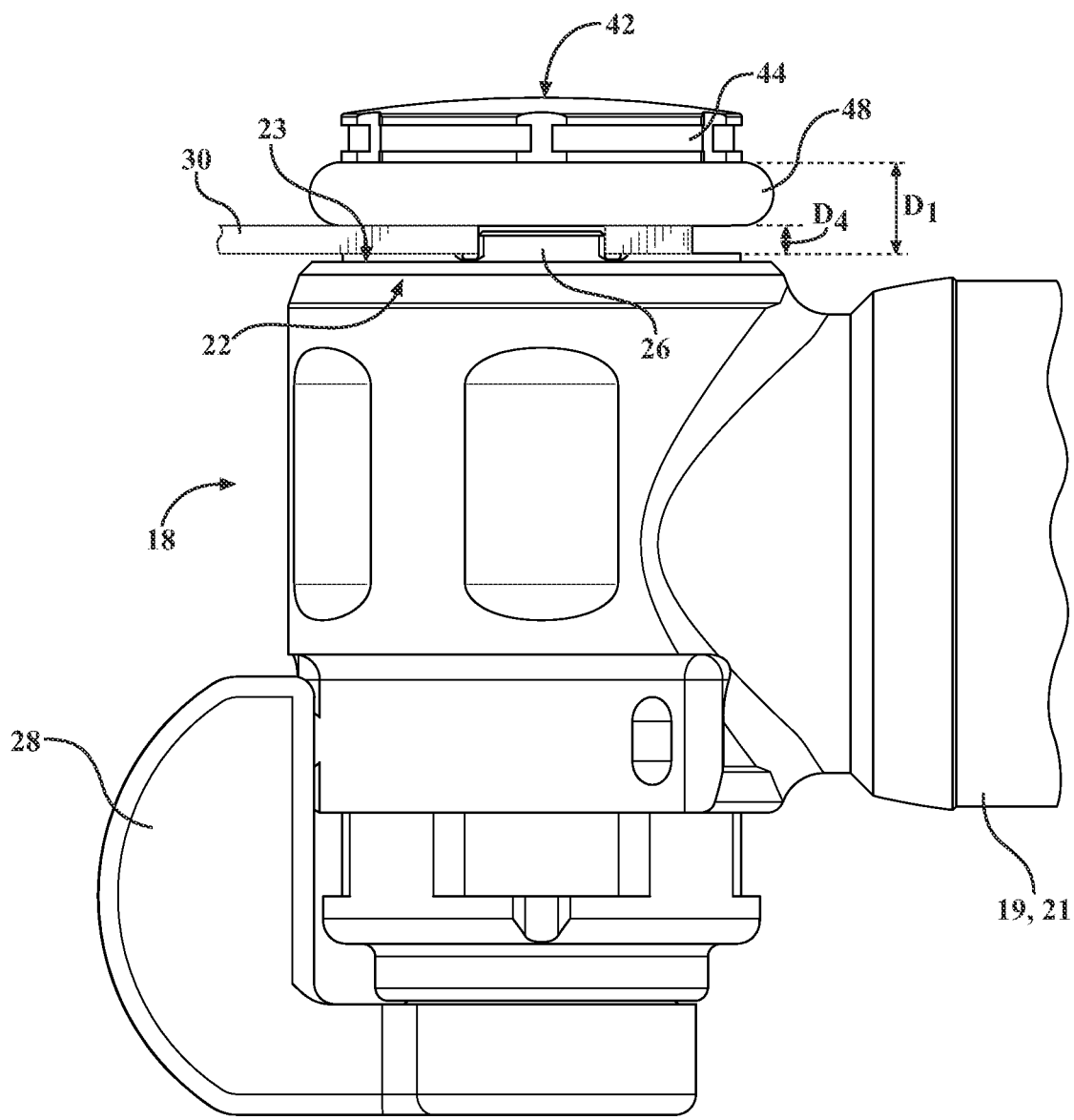
FIG. 6A is a side view of the blade mounting assembly including the blade clamp in the exposed position and the saw blade inserted into the blade mounting assembly, according to one implementation.
Figure 6B:
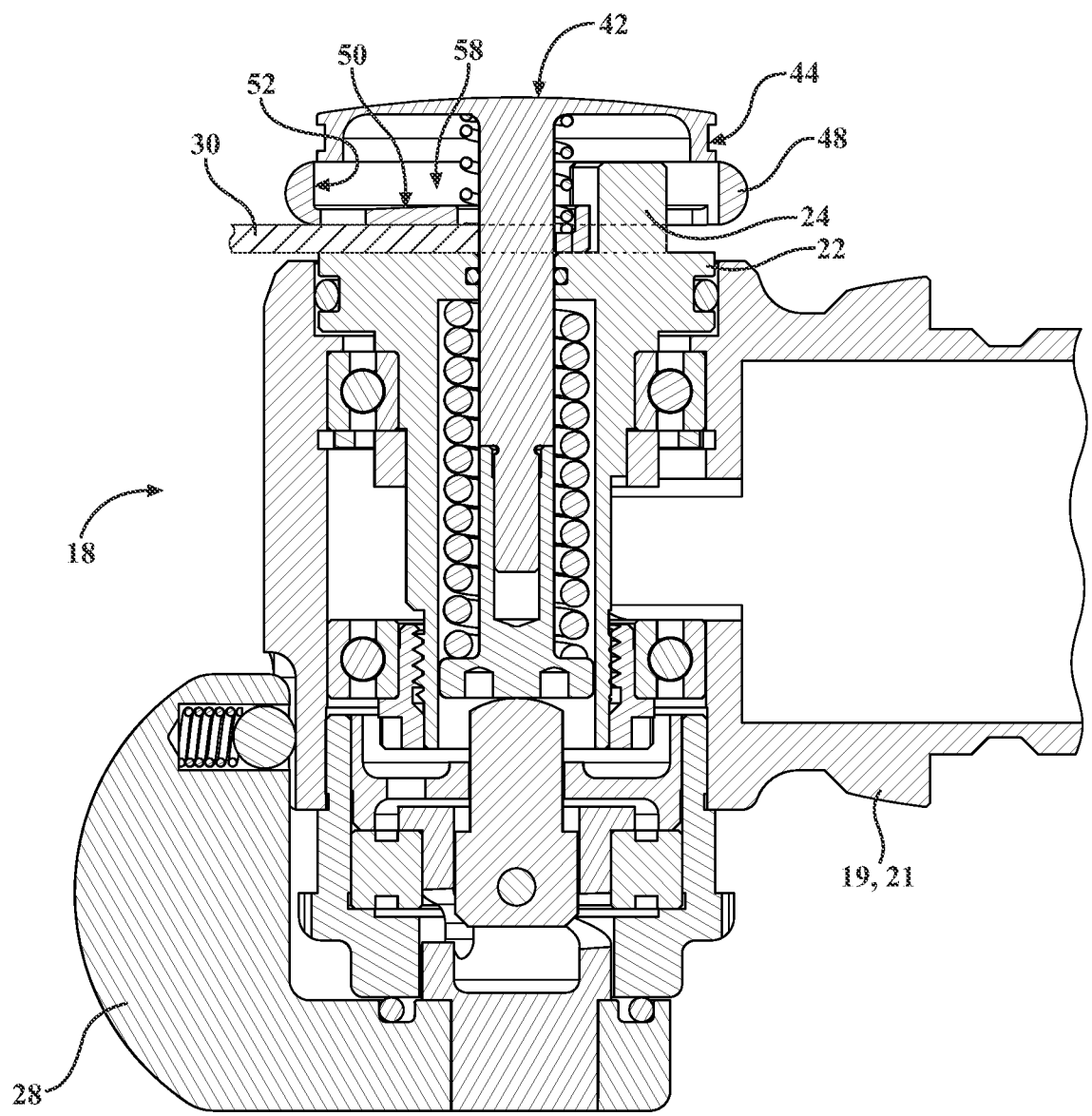
FIG. 6B is a sectional view of the blade mounting assembly and blade of FIG. 6A.

Referring to FIGS. 6A and 6B, an exemplary configuration of the blade mounting assembly 18 in a secured state is illustrated. Similar to in the at-rest state and the insertion state, the control mechanism 28 is in the open position and the blade clamp 42 is in the first position. At this point, the saw blade 30 has been fully inserted into the blade mounting assembly 18, with the attachment portion abutting the support surface 23 of the drive hub 22 and the drive bosses 24, 26 being seated within the central indent 38 and primary indent(s) 40 of the attachment portion of the blade, as described above. Once the attachment portion 32 is resting on the support surface 23 of the drive hub 22, the saw blade 30 is no longer exerting a force on the clamp guard opposite the biasing mechanism 46. This allows the biasing mechanism 46 to expand from its compressed stated (as experienced during the insertion state), urging the clamp guard 48 away from the blade clamp 42, causing the clamp guard 48 to hold the saw blade 30 in place within the blade mounting assembly 18. The force from the biasing mechanism causes the clamp guard 48 to be spaced a fourth distance D4 from the support surface 23 of the drive hub 22. Depending on the properties of the saw blade 30, such as the thickness of the attachment portion 32, the fourth distance D4 may be equal to or greater than the second distance D2 that the clamp guard 48 is spaced from the support surface 23 of the drive hub 22 in the at-rest state. For example, a thicker attachment portion 32 may result in the biasing mechanism 46 causing the clamp guard to abut the attachment portion 32 and being space the fourth distance D4 from the support surface 23 such that the fourth distance D4 is greater than the second distance D2. Alternatively, if the attachment portion 32 is sufficiently thin enough, the biasing mechanism 46 may cause the clamp guard 48 to be spaced a fourth distance D4 from the support surface 23 such that the fourth distance D4 is equal to the second distance D2. While the force applied by the biasing mechanism 46 can be overcome by the user applying a force to the saw blade 30 to insert and/or remove the saw blade 30, the force exerted on the clamp guard 48 by the biasing mechanism 46 is sufficient to hold the saw blade 30 within the blade mounting assembly 18 absent such additional force(s). One of the many advantages of such a configuration is that the clamp guard 48, in combination with the biasing mechanism 46, hold the saw blade 30 in place once it has been inserted in the blade mounting assembly 18 by the user. This can help prevent the saw blade 30 from falling out prior to the user fully securing the saw blade 30 in place by moving the blade clamp 42 to the second position. It can also prevent the saw blade 30 from becoming disengaged and/or misaligned with the drive boss(es) 24, 26 as the blade clamp 42 is moved from the first position to the second position. While the blade mounting assembly 18 is in the secured state, the blade clamp 42 remains protruded from the clamp guard 48 such that the safety indicator 44 remains visible to the user notifying them that the surgical saw assembly 10 is not safe for operation.

The clamp guard 48 also assists in preventing the user from pinching their finger or another extremity. The clamp guard 48, in combination with the biasing mechanism 46, reduces the distance and/or gap between the support surface 23 and the nearest point of contact, i.e. the clamp guard 48 or the blade clamp 42. For example, without the clamp guard 48, when the blade clamp 42 is in the first position, the distance between the support surface 23 and the bottom surface 45 of the blade clamp 42 would be the first distance D1. Alternatively, using the blade mounting assembly 18 described above including a clamp guard 48, the clamp guard 48 is spaced the second distance D2 from the support surface 23 when the blade clamp 42 is in the first position. The second distance D2 is less than the first distance, meaning there is less space for a finger or another objected to get wedged between the blade clamp 42 and the support surface 23, reducing the likely hood of something getting pinched when the blade clamp 42 is moved from the first position to the second position.

Figure 7A:
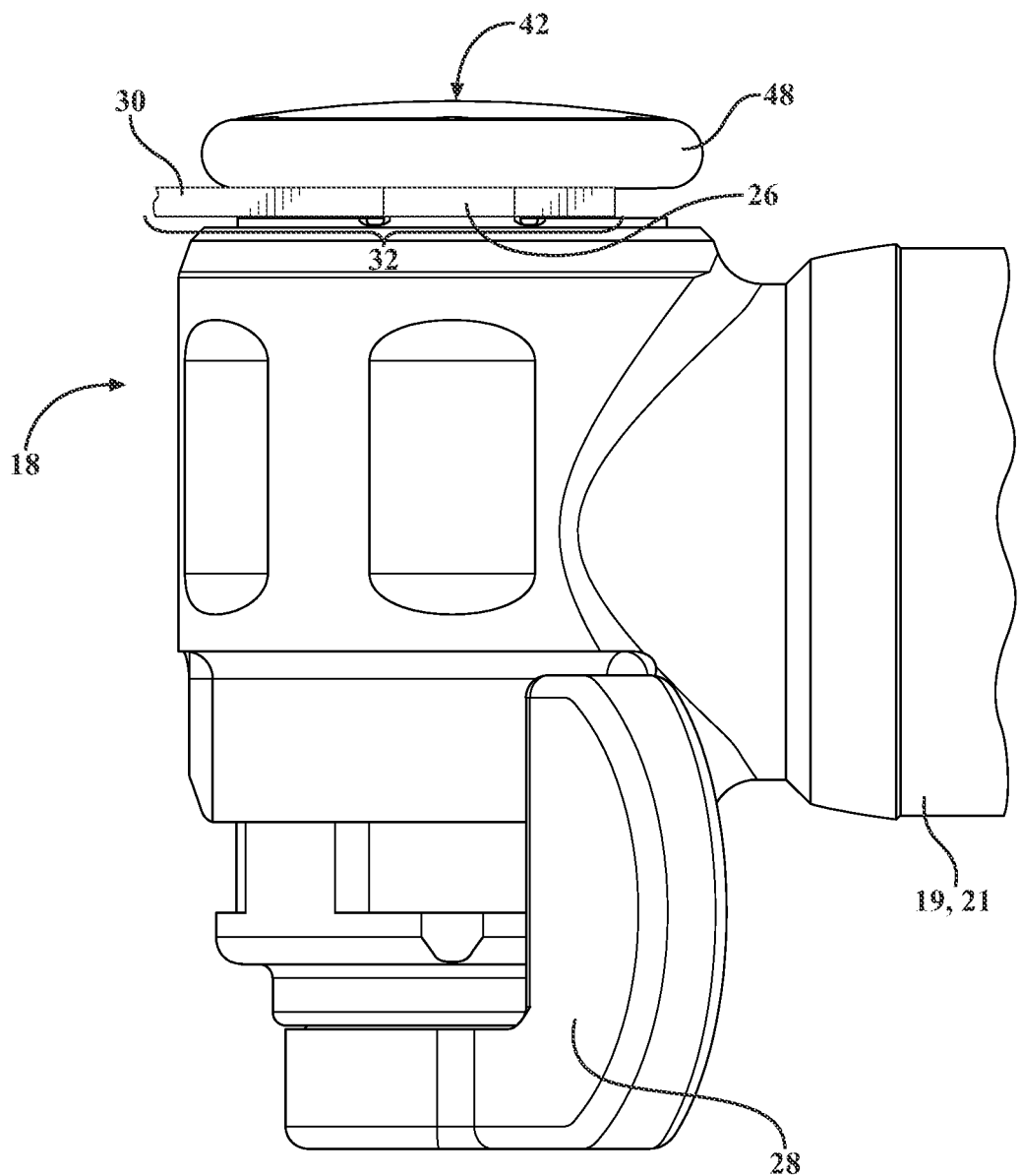
FIG. 7A is a side view of the blade mounting assembly including the blade clamp in the concealed position and the saw blade secured within the blade mounting assembly, according to one implementation.
Figure 7B:
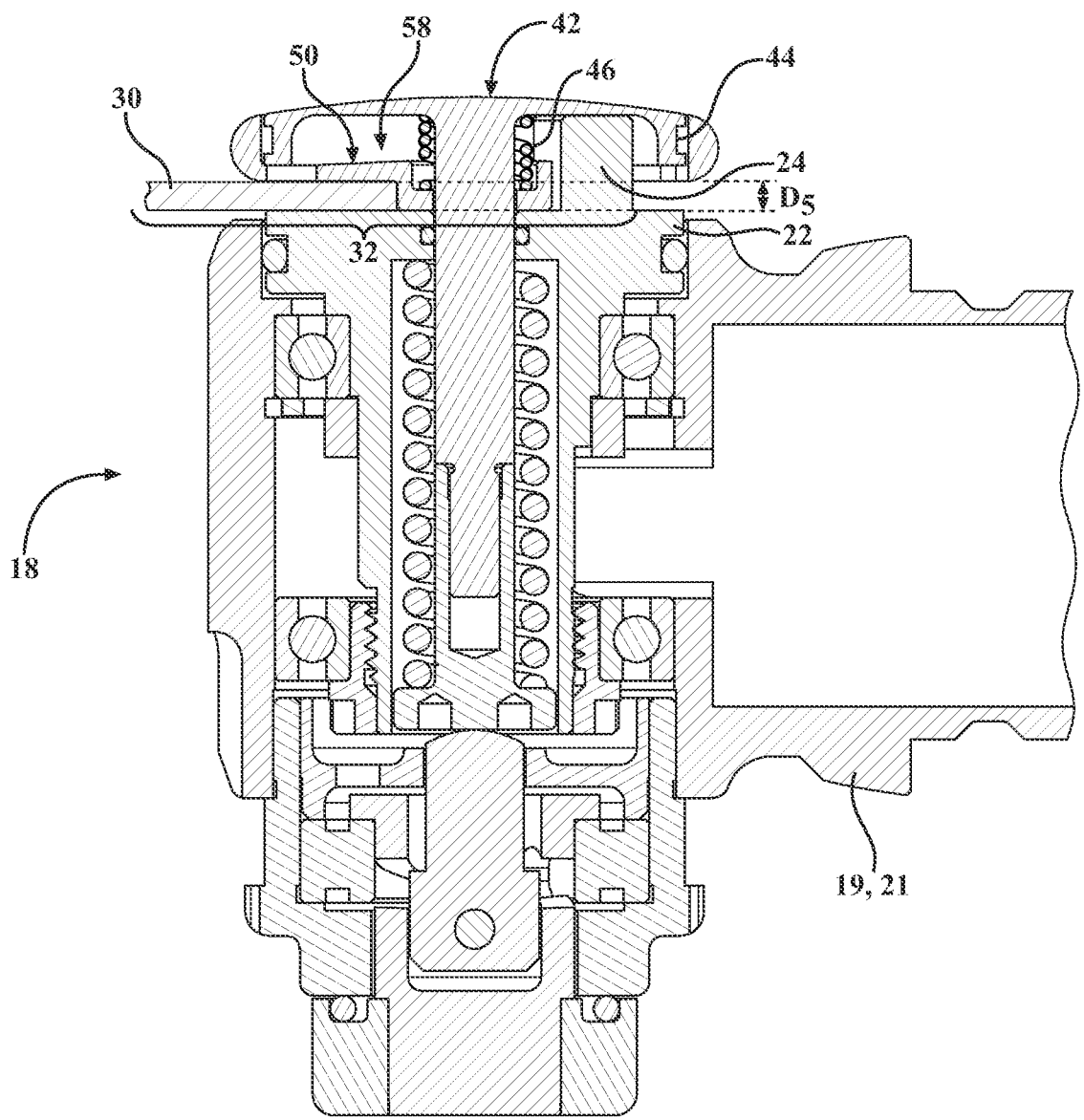
FIG. 7B is a sectional view of the blade mounting assembly and blade of FIG. 7A.

Referring to FIGS. 7A and 7B, an exemplary configuration of the blade mounting assembly 18 in a closed state is illustrated. The control mechanism 28 is in the closed position causing the blade clamp 42 to be in the second position. As described above, when the blade clamp 42 is in the second position, the blade clamp 42 is retracted and is spaced a fifth distance D5 from the support surface 23 of the drive hub 22. When the blade clamp 42 is retracted, the biasing mechanism 46 is compressed such that the blade clamp 42 is disposed within the recess 58 defined by the clamp guard 48. As the blade clamp 42 is disposed within the recess 58, the safety indicator 44 is concealed by the clamp guard 48. The absence of the presence of the safety indicator suggests to the user that the surgical saw assembly 10 is safe to operate. Furthermore, the blade clamp 42, in combination with the biasing mechanism 46, press the clamp guard 48 against the saw blade 30, locking the saw blade 30 within the blade mounting assembly 18.

As can be understood from the foregoing description, the blade mounting assembly provides technical solutions to several technical problems. For example, the blade mounting assembly prevents potential that a user can be pinched by the clamp during clamping. The clamp is encapsulated and non-exposed, and hence, the user is protected from the path of the clamping force. Furthermore, the clamp guard provides flexibility to move for easy accessory installation while providing an intermediate level of securing of the accessory prior to full clamping. Hence, the clamp guard eliminates extra spacing around the accessory thereby reducing potential that the accessory can be loosely mounted before clamping. The clamp guard also prevents the accessory from potentially falling out from the tool before clamping. Additionally, the safety indicator provides a user with clear indication of full and proper clamping of the accessory. The safety indicator reduces potential of the possibility of the user proceeding to operate the tool on the incorrect assumption that the accessory is properly secured.

Several configurations have been discussed in the foregoing description. However, the configurations discussed herein are not intended to be exhaustive or limit the invention to any particular form. The terminology which has been used is intended to be in the nature of words of description rather than of limitation. Many modifications and variations are possible in light of the above teachings and the invention may be practiced otherwise than as specifically described.

What is claimed is:

1. A mounting assembly of a surgical instrument for removable coupling of a surgical accessory to the surgical instrument, wherein the mounting assembly comprises:
   a support surface;
   an accessory clamp disposed above the support surface, the accessory clamp configured to be movable relative to the support surface between a first position and a second position;
   a clamp guard disposed between the support surface and the accessory clamp, the clamp guard including one or more surfaces that define a recess for receiving the accessory clamp, and wherein the one or more surfaces define an aperture configured to prevent accumulation of debris within the recess;
   a control mechanism manipulatable by the user to move the accessory clamp between the first position and the second position; and
   wherein the accessory clamp is configured to be at least partially disposed within the recess of the clamp guard when the accessory clamp is in the second position.

2. The mounting assembly of claim 1, whereby:
   in the first position, the accessory clamp is spaced apart from the support surface by a first distance; and
   in the second position the accessory clamp is spaced apart from the support surface by a second distance,
   wherein the second distance is less than the first distance.

3. The mounting assembly of claim 1, further comprising a boss extending above the support surface;
   wherein the aperture defined in the clamp guard is configured to receive the boss when the accessory clamp is in the second position.

4. The mounting assembly of claim 1, wherein the aperture defined by the one or more surfaces of the clamp guard is a plurality of apertures, the plurality of apertures configured to prevent accumulation of debris within the recess.

5. The mounting assembly of claim 4, wherein one or more surfaces of the clamp guard comprise a primary surface and a guard side surface that extends from a perimeter of the primary surface to define the recess of the clamp guard; and
   wherein the plurality of the apertures are defined by the primary surface proximate the perimeter of the primary surface where the guard side surface extends from the primary surface.

6. The mounting assembly of claim 1, further comprising a biasing mechanism disposed between the clamp guard and the accessory clamp, and wherein:
   in the first position, the biasing mechanism is configured to urge the clamp guard away from the accessory clamp such that the accessory clamp protrudes from the clamp guard; and
   in the second position, the biasing mechanism is configured to be compressed to allow the accessory clamp to be at least partially retracted within the recess of the clamp guard.

7. The mounting assembly of claim 6, wherein the support surface further comprises at least one drive member protruding from a plane of the support surface, the at least one drive member configured to actuate the surgical accessory when the support surface is actuated by a motor.

8. The mounting assembly of claim 7, whereby in the first position, the mounting assembly is configured to operate in an at-rest state when an attachment portion of the surgical accessory is not inserted into the mounting assembly, whereby in the at-rest state, the biasing mechanism is configured to urge the clamp guard away from the accessory clamp such that the clamp guard remains proximal the at least one drive member when the accessory clamp is spaced a first distance from the support surface.

9. The mounting assembly of claim 7, whereby in the first position, the mounting assembly is configured to operate in an insertion state when an attachment portion of the surgical accessory is partially inserted into the mounting assembly such that the attachment portion of the surgical accessory is wedged between the clamp guard and the at least one drive member, whereby in the insertion state, the biasing mechanism is configured to be compressed, allowing the clamp guard to move from being spaced a third distance from the support surface to a fourth distance from the support surface as the attachment portion is wedged between the clamp guard and the at least one drive member.

10. The mounting assembly of claim 7, whereby in the first position, the mounting assembly is configured to operate in a secured state when an attachment portion of the surgical accessory is fully inserted into the mounting assembly such that the attachment portion of the surgical accessory is supported by the support surface and coupled to the at least one drive member, whereby in the secured state, the biasing mechanism is configured to urge the clamp guard to directly abut the attachment portion of the surgical accessory against the support surface.

11. A surgical tool assembly comprising:
 a surgical accessory having an attachment portion;
 a housing;
 a motor disposed within the housing;
 an accessory mounting assembly removably coupled to the housing and configured to receive the attachment portion of the surgical accessory, the accessory mounting assembly comprising:
  a support surface configured to be actuated by the motor to drive the surgical accessory; and
  an accessory clamp disposed above the support surface and configured to move relative to the support surface between a first position and a second position;
  a clamp guard disposed between the support surface and the accessory clamp such that the attachment portion of the surgical accessory is disposed between the clamp guard and support surface when coupled to the accessory mounting assembly, the clamp guard including one or more surfaces that define a recess for receiving the accessory clamp, and wherein the one or more surfaces define an aperture configured to prevent accumulation of debris within the recess.

12. The surgical tool assembly of claim 11, further comprising a biasing mechanism disposed between the clamp guard and the accessory clamp, the biasing mechanism configured to urge the clamp guard away from the accessory clamp such that a distance between the clamp guard and the support surface remains substantially constant as the accessory clamp is moved between the first position and the second position; and
 wherein when the accessory clamp is in the first position, the accessory clamp is configured to be spaced apart from the clamp guard by a first distance and at least a portion of the accessory clamp protrudes from the recess of the clamp guard; and
 wherein when the accessory clamp is in the second position, the accessory clamp is configured to be spaced apart from the clamp guard by a second distance and the accessory clamp is at least partially disposed in the recess of the clamp guard.

13. The surgical tool assembly of claim 12, wherein the support surface further comprises at least one drive member protruding from a plane of the support surface, the at least one drive member configured to actuate the surgical accessory when the support surface is actuated by a motor; and
 wherein in the first position:
  the accessory mounting assembly is configured to operate in an at-rest state wherein the attachment portion of the surgical accessory is not inserted into the accessory mounting assembly; and
  in the at-rest state, the biasing mechanism is configured to urge the clamp guard away from the accessory clamp such that the clamp guard remains proximal the at least one drive member when the accessory clamp is spaced the first distance from the support surface.

14. The surgical tool assembly of claim 12, wherein the support surface further comprises at least one drive member protruding from a plane of the support surface, the at least one drive member configured to actuate the surgical accessory when the support surface is actuated by a motor; and
 wherein in the first position:
  the accessory mounting assembly is configured to operate in an insertion state wherein the attachment portion of the surgical accessory is partially inserted into the accessory mounting assembly such that the attachment portion of the surgical accessory is wedged between the clamp guard and the at least one drive member; and
  in the insertion state, the biasing mechanism is configured to be compressed allowing the clamp guard to move from being spaced a third distance from the support surface to a fourth distance from the support surface as the attachment portion is wedged between the clamp guard and the at least one drive member.

15. The surgical tool assembly of claim 12, wherein the support surface further comprises at least one drive member protruding from a plane of the support surface, the at least one drive member configured to actuate the surgical accessory when the support surface is actuated by a motor; and
 whereby in the first position, the accessory mounting assembly is configured to operate:
  in an at-rest state, wherein the attachment portion of the surgical accessory is not inserted into the accessory mounting assembly, whereby in the at-rest state, the biasing mechanism is configured to be compressed to a fifth distance between the clamp guard and the accessory clamp;
  in an insertion state, wherein the attachment portion of the surgical accessory is partially inserted into the accessory mounting assembly such that the attachment portion of the surgical accessory is wedged between the clamp guard and the at least one drive member, whereby in the insertion state, the biasing mechanism is configured to be compressed to a sixth distance between the clamp guard and the accessory clamp, wherein the sixth distance is less than the fifth distance; and
  in a secured state, wherein the attachment portion of the surgical accessory is fully inserted into the accessory mounting assembly such that the attachment portion of the surgical accessory is supported by a platform and coupled to the at least one drive member, whereby in the secured state, the biasing mechanism is configured to be compressed to a seventh distance between the clamp guard and the accessory clamp, wherein the seventh distance is less than or equal to the fifth distance.

16. The surgical tool assembly of claim 11, wherein the accessory clamp comprises an upper surface, a lower surface and a clamp side surface disposed between the upper and the lower surfaces;
 a safety indicator is disposed along the clamp side surface of the accessory clamp, the safety indicator configured such that the safety indicator is exposed by the clamp guard when the accessory clamp is in the first position and the safety indicator is concealed by the clamp guard when the accessory clamp is in the second position.

17. The surgical tool assembly of claim 11, further comprising a boss extending above the support surface;

wherein the aperture defined in the clamp guard is configured to receive the boss when the accessory clamp is in the second position.

18. The surgical tool assembly of claim 11, wherein the one or more surfaces of the clamp guard comprise a primary surface and a guard side surface that extends from a perimeter of the primary surface to define the recess of the clamp guard;

wherein the aperture defined by the clamp guard is a plurality of apertures, the plurality of apertures configured to prevent accumulation of debris within the recess; and wherein the plurality of the apertures are defined by the primary surface proximate the perimeter of the primary surface where the guard side surface extends from the primary surface.

19. A mounting assembly of a surgical instrument for removable coupling of a surgical accessory to the surgical instrument, wherein the mounting assembly comprises:

a support surface;

an accessory clamp disposed above the support surface and the accessory clamp configured to be movable relative to the support surface between a first position and a second position;

a clamp guard disposed between the support surface and the accessory clamp, the clamp guard including one or more surfaces that define a recess for receiving the accessory clamp, and wherein the one or more surfaces define an aperture configured to prevent accumulation of debris within the recess;

a control mechanism manipulatable by the user to move the accessory clamp between the first position and the second position; and wherein the accessory clamp is configured to be at least partially disposed within the recess of the clamp guard when the accessory clamp is in the second position.

20. The mounting assembly of claim 19, wherein one or more surfaces of the clamp guard comprises a primary surface and a guard side surface that extends from a perimeter of the primary surface to define the recess of the clamp guard; and wherein the aperture is defined by the primary surface proximate the perimeter of the primary surface where the guard side surface extends from the primary surface.

* * * * *